(12) United States Patent
Bryant et al.

(10) Patent No.: US 10,571,413 B2
(45) Date of Patent: Feb. 25, 2020

(54) METHOD FOR CHECKING AN ELECTRONIC COMPONENT

(71) Applicant: YXLON INTERNATIONAL GMBH, Hamburg (DE)

(72) Inventors: Keith Bryant, Johannesburg (ZA); Bernhard Murkens, Hamburg (DE); Mathias Wientapper, Hamburg (DE)

(73) Assignee: YXLON INTERNATIONAL GMBH, Hamburg (DE)

( * ) Notice: Subject to any disclaimer, the term of this patent is extended or adjusted under 35 U.S.C. 154(b) by 75 days.

(21) Appl. No.: 15/564,311

(22) PCT Filed: Apr. 14, 2016

(86) PCT No.: PCT/EP2016/000612
§ 371 (c)(1),
(2) Date: Oct. 4, 2017

(87) PCT Pub. No.: WO2016/165828
PCT Pub. Date: Oct. 20, 2016

(65) Prior Publication Data
US 2018/0136145 A1     May 17, 2018

(30) Foreign Application Priority Data

Apr. 15, 2015  (DE) .................. 10 2015 004 650
May 5, 2015    (DE) .................. 10 2015 005 641

(51) Int. Cl.
*G01N 23/18*       (2018.01)
*G06T 7/00*        (2017.01)
(Continued)

(52) U.S. Cl.
CPC .......... *G01N 23/18* (2013.01); *G06K 7/1413* (2013.01); *G06T 7/001* (2013.01); *G06T 7/0004* (2013.01);
(Continued)

(58) Field of Classification Search
CPC .................. G01N 23/18; G01N 21/95; G01N 2021/95638; G01N 2223/6113;
(Continued)

(56) References Cited

U.S. PATENT DOCUMENTS

| 5,369,431 A | * | 11/1994 | Levy | ................. | G01R 31/2808 |
| | | | | | 348/126 |
| 6,269,179 B1 | * | 7/2001 | Vachtsevanos | ........ | G01N 21/88 |
| | | | | | 348/126 |

(Continued)

FOREIGN PATENT DOCUMENTS

| CN | 1729799 A | 2/2006 |
| CN | 101759139 A | 6/2010 |

OTHER PUBLICATIONS

Aurthor: Stig Oresjo, Title: When to Use AOI, When to Use AXI, and When to Use Both, date: Dec. 2002, Published: Nepcon West (Year: 2002).*

(Continued)

*Primary Examiner* — Taeho Jo
(74) *Attorney, Agent, or Firm* — Abelman, Frayne & Schwab

(57) ABSTRACT

The invention relates to a method for testing an electronic component for defects, by examining the electronic component in a production line by means of automatic optical inspection; determining the coordinates of regions in which an examination using automatic optical inspection is not possible; transmitting the coordinates of these regions from the production line to a computer; transporting the electronic component from the production line into an X-ray device which is arranged outside the production line, for non-destructive material testing; transmitting the coordinates of the regions from the computer to this X-ray device; examining the electronic component by means of the X-ray device only in the regions in which an examination using (Continued)

automatic optical inspection is not possible; transmitting the results of the examination in the X-ray device to the computer; returning the electronic component to the production line if the result indicates that it is not defective.

16 Claims, 1 Drawing Sheet

(51) Int. Cl.
  *G06K 7/14* (2006.01)
  *G01N 21/956* (2006.01)
  *G01N 21/95* (2006.01)
(52) U.S. Cl.
  CPC ... *G01N 21/95* (2013.01); *G01N 2021/95638* (2013.01); *G01N 2223/6113* (2013.01); *G01N 2223/66* (2013.01); *G06T 2207/10116* (2013.01); *G06T 2207/30141* (2013.01)
(58) Field of Classification Search
  CPC .............. G01N 2223/66; G06K 7/1413; G06T 7/0004; G06T 7/001; G06T 2207/10116; G06T 2207/30141
  USPC ................................................ 378/58, 57, 59
  See application file for complete search history.

(56) References Cited

U.S. PATENT DOCUMENTS

| | | | | |
|---|---|---|---|---|
| 7,991,214 | B1* | 8/2011 | Choi | G06T 7/0004 250/302 |
| 9,612,284 | B2* | 4/2017 | Gu | G01R 31/31705 |
| 2001/0028732 | A1* | 10/2001 | Coulombe | G06T 7/0006 382/149 |
| 2002/0072822 | A1* | 6/2002 | Raymond | G01R 31/2806 700/108 |
| 2004/0004482 | A1* | 1/2004 | Bouabdo | G01R 31/2846 324/501 |
| 2004/0028267 | A1* | 2/2004 | Shoham | G01N 21/93 382/141 |
| 2004/0068702 | A1* | 4/2004 | Parker | G01R 31/31835 716/106 |
| 2005/0225754 | A1* | 10/2005 | Ume | G01N 21/95607 356/237.1 |
| 2005/0281452 | A1* | 12/2005 | Usikov | G06K 9/4642 382/141 |
| 2007/0075050 | A1* | 4/2007 | Heyl | B23K 26/03 219/121.6 |
| 2007/0189451 | A1* | 8/2007 | Lee | G01N 21/95607 378/51 |
| 2008/0083816 | A1* | 4/2008 | Leinbach | B23K 3/0638 228/102 |
| 2008/0096294 | A1* | 4/2008 | Liu | H01L 22/24 438/16 |
| 2009/0268869 | A1* | 10/2009 | Hadland | G01N 23/046 378/58 |
| 2010/0074405 | A1* | 3/2010 | Saito | G01N 23/223 378/44 |
| 2011/0080998 | A1* | 4/2011 | Saito | G01N 23/223 378/50 |
| 2012/0015457 | A1* | 1/2012 | Rawlinson | H01L 24/75 438/15 |
| 2014/0010952 | A1* | 1/2014 | Rosenstein | H05K 3/0085 427/8 |
| 2014/0043033 | A1* | 2/2014 | Butters | G01R 31/2656 324/501 |
| 2014/0119511 | A1* | 5/2014 | Ward | G01N 23/20 378/71 |
| 2015/0066180 | A1* | 3/2015 | Qian | G05B 19/418 700/98 |
| 2018/0101945 | A1* | 4/2018 | Stone | G06T 7/0004 |
| 2019/0227001 | A1* | 7/2019 | Cho | G01R 31/311 |

OTHER PUBLICATIONS

Chinese text of 1st Office Action dated Oct. 9, 2019 and which lists prosecution search results for Chinese Appl'n No. CN 201680021844.1.

* cited by examiner

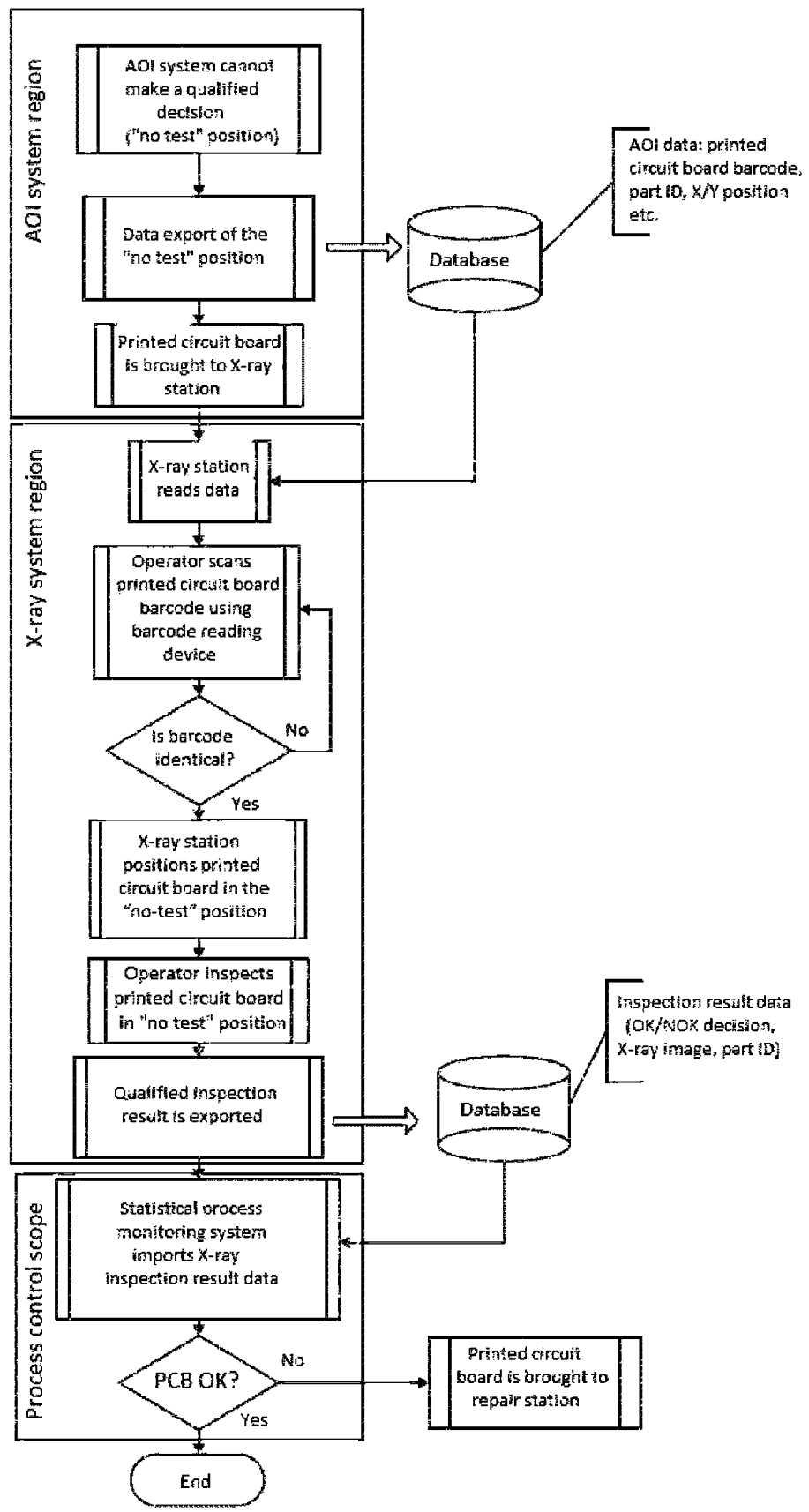

METHOD FOR CHECKING AN ELECTRONIC COMPONENT

CROSS-REFERENCE TO RELATED APPLICATIONS

This application claims priority to PCT/EP2016/000612, filed 14 Apr. 2016, which claims benefit to German Application No. 102015004650.0 filed on 15 Apr. 2015, and to German Application No. 102015005641.7, filed on 5 May 2015.

BACKGROUND OF THE INVENTION

Field of the Invention

The invention relates to a method for testing an electronic component for defects, in which both an automatic optical inspection (AOI) and non-destructive material testing (NDT) by means of X-radiation are carried out.

By "electronic components" in the context of this invention is meant, among other things, printed circuit board assemblies, wafers—silicon slices with etched structures such as for example micro solder balls—and electronic components, such as for example semiconductors and LEDs.

Description of Related Art

In principle, the testing of a printed circuit board assembly—hereafter printed circuit board assemblies will be referred to simply as circuit boards—and of a wafer or of a receiving tray for components is the same. The difference between the testing of a circuit board and a wafer or an electronic component, for example a semiconductor, is essentially that the wafer or the component is clearly positioned in a firmly predefined holder—a kind of receiving tray. This holder can for example be in the form of a rectangular tray, analogous to the rectangular geometry of a circuit board. Several wafers or electronic components can be positioned on one receiving tray.

For simplification, statements are only made for circuit boards below; however, these always also apply equally to wafers or electronic components arranged in a receiving tray, unless explicitly indicated otherwise at individual points.

When testing circuit boards for defects, it is known to examine the circuit boards within the production line by means of an AOI. Errors in the alignment of the components affixed to the circuit board or defects of the solder connections between the circuit board and the components connected thereto are detected here. The possible defects include for example solder bridges, missing solder connections, and solder connections with porosities. However, during optical examination by means of AOI, it is only possible to find defects that are visible from the outside; hidden defects cannot be detected therewith. In order to be able to recognize these defects, the circuit board is subjected to an NDT method using X-radiation, in addition to the AOI. The non-visible points are examined by means of radioscopy without damaging the circuit board. From a combination of the results of the AOI and the X-ray NDT, it can then be decided whether the circuit board can continue in the production line, or whether it is a reject or has to be subjected to reworking.

This combined testing with AOI and X-ray NDT can either be carried out in that the X-ray NDT test device is integrated in the production line, or is arranged separate therefrom. In the first alternative with integrated X-ray NDT test device, it is problematic that the entire production line is at a standstill when maintenance or repair operations have to be carried out on the X-ray NDT test device; moreover each production line needs its own X-ray NDT test device, giving rise to very high costs for the entire production line.

In the second alternative with separately arranged X-ray NDT test device, the costs per production line are lower, as a single X-ray NDT test device can be used for two or more production lines. However, testing in a separate X-ray NDT test device is time-consuming, as the circuit board has to be brought into the X-ray NDT test device from the production line, and the entire circuit board has to be re-examined there, this time with X-radiation instead of light.

BRIEF SUMMARY

The object of the invention is therefore to provide a method which, for the second alternative with separate X-ray NDT test device, makes a shorter test time in the X-ray NDT test device possible.

This object is achieved by a method with the features of claim 1. The method according to the invention provides that, in the production line, during the performance of the AOI, the coordinates of the regions in which no statement can be made about the state of the electronic component by means of light are determined. The coordinates of the individual regions that have been found in this way, which are called regions of interest (ROIs), are transmitted to a computer. After the electronic component has been transported from the production line into the X-ray device for non-destructive material testing—called X-ray NDT test device above, and shortened to X-ray device below—only the ROIs are examined by means of X-radiation. For this purpose, the coordinates of the ROIs detected in the AOI have been transmitted from the computer to the X-ray device. This saves an enormous amount of time, as the entire electronic component no longer has to be irradiated by means of X-radiation—i.e. also the regions which have already been tested for defects by means of the AOI—but only the ROIs, i.e. the regions about which no statement can be made by means of the AOI with respect to the presence of defects. The results of the X-ray examination of the ROIs are then transmitted to the computer, so that the result can be reproduced there and statistics relating to the production process and any defects can be created.

An advantageous development of the invention provides that the electronic component has an identifier by means of which the electronic component is clearly identifiable, and this identifier is transmitted to the computer from the production line to the X-ray device together with the coordinates of the regions in which an examination using automatic optical inspection is not possible, and the identifier is detected in the X-ray device, and these data are transmitted to the computer, where the data are compared with the identifier from the production line and the X-ray device. An easy and clear alignment of the electronic component in the X-ray device, is thereby made possible, with the result that the coordinates of the ROIs previously determined in the AOI can be approached accurately.

Preferably, the identifier is a barcode which is detected in the X-ray device by a barcode reading device. It is hereby simply and reliably ensured that the electronic component, for which the questionable data have been obtained in the AOI, is the same one that is now subjected to the X-ray examination. It is thus also ensured that the correct ROIs for the electronic component currently located in the X-ray device are examined.

A further advantageous development of the invention provides that the transport and/or the return of the electronic component between production line and X-ray device takes place automatically. Any source of faults due to a manual removal of the electronic component from the production line, carrying the electronic component from the production line into the X-ray device and manual insertion and alignment therein is thereby eliminated.

A further advantageous development of the invention provides that the coordinates of the regions in which an examination using automatic optical inspection is not possible are determined with respect to a location which has a clear feature of the electronic component, for example a corner of the circuit board or receiving tray or a characteristic hole. The alignment of the electronic component preferably takes place in the X-ray device with reference to the location of the clear feature of the electronic component. It is thereby ensured with certainty that an accurate approach of the ROIs can take place based on the coordinates found in the AOI.

A further advantageous development of the invention provides that, by the examination in the X-ray device, the type of an established defect is obtained and, with this information, a control of the process takes place in the production line to avoid the type of defect. Thus, it is possible to intervene in the production process when it becomes clear that a defect is not just an isolated occurrence, but a trend towards such a fault can be established. A high reject rate is thus avoided and the production costs lowered.

The electronic component is preferably a printed circuit board assembly, a (silicon) wafer with etched structures, such as for example forms for micro solder balls, or an electronic component, such as for example a semiconductor or an LED.

A further advantageous development of the invention provides that, in the X-ray device, an open microfocus tube is used, in particular one with a target output of more than 10 watts. By the use of an open microfocus tube in the X-ray device, unlike with the use of conventional closed microfocus tubes—which are characterized by a fault detectability of approximately 3-10 μm, a detail detectability of up to 0.1 μm can be achieved. A further positive effect results in that open microfocus tubes with a high target output—certain producers now already offer X-ray tubes with up to 15 watt target output—instead of on average a maximum of 3 watts in the case of closed microfocus tubes, allow a substantially better fault detectability of, for example, porosities in solder balls; this applies in particular in the case of low-contrast test objects, such as for example certain electronic components. Current imaging X-ray NDT systems in the inline testing of electronic components predominantly use tubes of the closed type which have the result that some of the faults described here are not recognized, or not correctly recognized, which can lead to an increased reject rate or, at worst, to production faults being overlooked.

Further advantages and details of the invention are explained below with reference to the embodiment example shown in the FIGURE. For simplification, only the testing of a circuit board is explicitly discussed; for other electronic components, such as for example wafers or electronic components, the following likewise applies, unless explicitly stated otherwise at individual points.

BRIEF DESCRIPTION OF THE DRAWINGS

The single FIGURE shows a flow chart of a method according to the invention.

DETAILED DESCRIPTION

The FIGURE shows a flow chart of an embodiment example of a method according to the invention for testing a circuit board. The steps of an AOI system are shown in the top rectangle, the steps of an (NDT) X-ray device in the middle rectangle, and the steps for deciding what is to happen with the tested circuit board in the bottom rectangle.

The first step in the top rectangle in the context of the AOI testing within a production line is the result of the preceding AOI testing of the circuit board; regions on the circuit board have been determined, in which no statement can be made about the presence or absence of defects of the circuit board in the context of the AOI examination by means of light. This can be the case for a number of reasons, such as for example concealed faults which can only be detected in the X-ray image. Typical undetectable faults in the AOI are for example porosities in solder bridges, unclosed contactings of the solder connections between a component—such as a microchip—and the circuit board. Typical undetectable faults in electronic components such as microchips are porosities in micro solder balls. Typical faults in wafers are incompletely etched structures of for example micro solder ball forms.

In the next step in the top rectangle, the coordinates of these regions in which an examination of the circuit board cannot be carried out by means of AOI are transmitted to a database in a computer. The transmitted data include information relating to a barcode which is applied to the circuit board and through which a clear identification of the circuit board just tested is possible, as well as an ID number assigned to the circuit board. Moreover, the coordinates (x/y coordinates in the plane of the circuit board, or a plane parallel thereto) of the above-named regions are transmitted. These coordinates relate to a point clearly identifiable on the circuit board, for example one of the corners of the circuit board or a characteristic hole in the circuit board; CAD data can also be referred to, if present. If it is not a circuit board that is being tested, but a wafer or an electronic component, the entire receiving tray receives a barcode which is arranged on the receiving tray. The identification of the individual components that are optionally present on the receiving tray can for example take place via automated serial numbering by the software on the receiving tray.

As a last step, in the top rectangle, the circuit board is moved from the production line into an X-ray device, which is arranged outside the production line; this X-ray device, in which an NDT method is carried out, in particular by means of radioscopy, can optionally be used for testing circuit boards from different production lines. The transport of the circuit board from the production line can either take place manually or by means of an automatic removal from the production line with automatic conveying of the circuit board into the X-ray device.

In the middle rectangle, the steps that are carried out in the context of the NDT testing in the X-ray device are shown.

In the first step, the information from the computer's database required for testing the circuit board is transmitted to the X-ray device. This includes the ID number of the circuit board already mentioned above, its barcode and the coordinates of the regions in which no AOI method could be carried out. The positioning of the circuit board in the X-ray device takes place with reference to the clear reference points on the circuit board, already described above, such as for example one of the corners of the circuit board, a characteristic hole in the circuit board or the CAD data of the circuit board.

In the second step in the middle rectangle, the barcode of the circuit board is scanned by means of a barcode scanner and after that compared with the information from the database. If it is established that there is no match, the scan is then repeated in order to check a faulty reading. In the unlikely event that an incorrect circuit board has been supplied, this is excluded from the testing process. If there is a match, the coordinates of the regions, in which no statements could be made by means of the AOI method about any defects present, transmitted from the computer's database are approached. In each of these regions, radioscopy is carried out by means of X-radiation in the context of an NDT method. The NDT method is not carried out over the entire circuit board, but only in the regions previously determined in the AOI method, whereby the time required for the NDT testing is significantly reduced. If it is not a circuit board that is being tested, but a wafer or an electronic component, the identification of an entire receiving tray takes place via the barcode on the receiving tray. The identification of the individual components that are optionally present on the receiving tray can take place via the automated serial numbering by the software on the receiving tray, already mentioned above.

In the penultimate step in the middle rectangle, one of the alternative types of inspection is indicated: an operator carries out a visual inspection and decides whether there is a defect in the region just examined, and optionally, what type of defect there is, for example defects in solder bridges, porosities in the solder connection, or missing contactings of the solder balls of the circuit board with the component.

These results—i.e. qualified statements about the examination result in the respective region tested—which include, among other things, a statement as to whether or not a defect is present, as well as the X-ray image and the ID number of the circuit board, are, according to the last step in the middle rectangle, transmitted to the database in the computer and stored there. Alternatively to the inspection by means of an operator, an automatic defect recognition (ADR) can also be carried out, whereby the above-mentioned results are obtained without needing the involvement of an operator; these results are then transmitted to the database—analogously to the procedure with operator.

The data contained in the database, relating to the circuit board, are used for the steps shown in the bottom rectangle. In the first step, the above-named data from the NDT method relating to the circuit board are transmitted from the computer's database to a process control system. Then, in a second step, this process control system takes the decision as to whether the circuit board is in order to the extent that—smaller defects can by all means still lead to a positive result with respect to the usability of the circuit board—it can be returned to the production line and production continues. If this is the case, the testing method according to the invention is ended with a return of the circuit board to the production line.

Should the defects found be so serious that the circuit board cannot be used, it is decided either that the circuit board is completely unusable—i.e. a reject—or it has to be subjected to reworking. Should reworking be necessary, as a rule the method according to the invention is carried out once again after the reworking, in order to be able to decide whether the circuit board can then be returned to the production line.

By the use of an open microfocus tube in the X-ray device, unlike with the use of conventional closed microfocus tubes—which are characterized by a fault detectability of approximately 3-10 μm, a detail detectability of up to 0.1 μm is achieved; this applies in particular in the case of a target output of more than 10 watts. An open microfocus tube with a high target output in the region of 15 watts— instead of on average a maximum of 3 watts in the case of closed microfocus tubes—brings a substantially better fault detectability of, for example, porosities in solder balls; this applies in particular in the case of low-contrast test objects, such as for example certain electronic components. Current imaging X-ray NDT systems in the inline testing of electronic components predominantly use tubes of the closed type which have the result that some of the faults described here are not recognized, or not correctly recognized, which can lead to an increased reject rate or, at worst, to production faults being overlooked. A clear improvement or remedy is achieved here by the invention.

The invention claimed is:

1. A method for testing an electronic component for defects
   comprising the steps of:
   performing a first examination of the electronic component in a production line by automatic optical inspection;
   determining location coordinates of one or more regions of the electronic component in which the automatic optical inspection during the first examination is not possible;
   transmitting the coordinates of the one or more regions from the production line to a computer;
   transporting the electronic component from the production line into an X-ray device which is arranged outside the production line, for non-destructive material testing;
   transmitting the coordinates of the one or more regions from the computer to the X-ray device;
   performing a second examination of the electronic component by the X-ray device based on the coordinates and only at the one or more regions in which the first examination using automatic optical inspection is not possible;
   transmitting results of the second examination in the X-ray device to the computer; and
   returning the electronic component to the production line if the results of the second examination indicate that the electronic component is not defective.

2. The method according to claim 1, wherein the electronic component has an identifier which is transmitted to the computer from the production line to the X-ray device together with the coordinates of the one or more regions in which the first examination using automatic optical inspection is not possible, and the identifier is detected in the X-ray device, and the data are transmitted to the computer, where the data are compared with the identifier from the production line and the X-ray device.

3. The method according to claim 2, wherein the identifier is a barcode which is detected in the X-ray device by a barcode reading device.

4. The method according to claim 1, wherein at least one of the transport and the return of the electronic component between production line and X-ray device takes place automatically.

5. The method according to claim 1, wherein the coordinates of the one or more regions in which the first examination using automatic optical inspection is not possible are determined with respect to a location which has a clear feature of the electronic component.

6. The method according to claim 5, wherein the alignment of the electronic component or of the receiving tray takes place in the X-ray device with reference to the location of the clear feature of the circuit board.

7. The method according to claim 5, wherein the clear feature of the electronic component is a corner of a circuit board.

8. The method according to claim 5, wherein the clear feature of the electronic component is a corner of a receiving tray.

9. The method according to claim 5, wherein the clear feature of the electronic component is a characteristic hole.

10. The method according to claim 1, wherein by the second examination in the X-ray device, a type of an established defect is obtained and, with this information, a control of the process takes place in the production line to avoid the type of defect.

11. The method according to claim 1, wherein the electronic component is at least one of a printed circuit board assembly, a wafer with etched structures and micro solder balls, and an electronic component.

12. The method according to claim 11, wherein the electronic component is a semiconductor.

13. The method according to claim 11, wherein the electronic component is an LED.

14. The method according to claim 1, wherein, in the X-ray device, an open micro-focus tube is used.

15. The method according to claim 14, wherein, in the micro-focus tube has a target output of more than 10 watts.

16. The method according to claim 1, wherein the second examination is a radioscopic examination of the electronic component.

* * * * *